(12) United States Patent
Del Guercio

(10) Patent No.: US 6,280,425 B1
(45) Date of Patent: Aug. 28, 2001

(54) EXTERNAL URINARY CATHETER

(76) Inventor: Edmund Del Guercio, 7 Forest Lake Dr., Media, PA (US) 19063

(*) Notice: Subject to any disclaimer, the term of this patent is extended or adjusted under 35 U.S.C. 154(b) by 0 days.

(21) Appl. No.: 08/985,835

(22) Filed: Dec. 5, 1997

(51) Int. Cl.$^7$ ............................. A61M 1/00; A47K 11/00
(52) U.S. Cl. ..................... 604/327; 604/349; 600/574; 4/144.3
(58) Field of Search ................... 604/327–331, 604/349–353; 4/144.1–144.4; 600/574

(56) References Cited

U.S. PATENT DOCUMENTS

| | | | |
|---|---|---|---|
| 3,703,731 | * 11/1972 | Leiser | 4/144.3 |
| 4,202,058 | * 5/1980 | Anderson | 4/144.3 |
| 4,484,917 | 11/1984 | Blackmon . | |
| 4,563,183 | 1/1986 | Barrodale et al. . | |
| 4,771,484 | * 9/1988 | Mozell | 4/144.3 |
| 4,976,692 | 12/1990 | Atad . | |
| 5,002,541 | * 3/1991 | Conkling et al. | 604/319 |
| 5,045,078 | 9/1991 | Asta . | |
| 5,147,315 | 9/1992 | Weber . | |
| 5,285,532 | * 2/1994 | Sealy | 4/144.3 |
| 5,295,983 | * 3/1994 | Kubo | 4/144.3 |
| 5,331,689 | * 7/1994 | Haq | 4/144.1 |
| 5,364,375 | 11/1994 | Swor . | |
| 5,632,736 | * 5/1997 | Block | 604/352 |

* cited by examiner

Primary Examiner—Dennis Ruhl
(74) Attorney, Agent, or Firm—Dilworth Paxson LLP

(57) ABSTRACT

An external catheter for attachment to the urethra is disclosed which includes a flow tube having a first and second end, the flow tube at the first end being funnel shaped, a spongy covering attached to the funnel shaped end for sealing an area around the urethra, said spongy covering being shaped so as to conform to the area surrounding the urethra, a skin adhesive for securing the spongy covering to the area surrounding the urethra and a fluid collector connected to said second end of said flow tube.

12 Claims, 4 Drawing Sheets

EXTERNAL URINARY CATHETER

FIELD OF THE INVENTION

Figure 1:
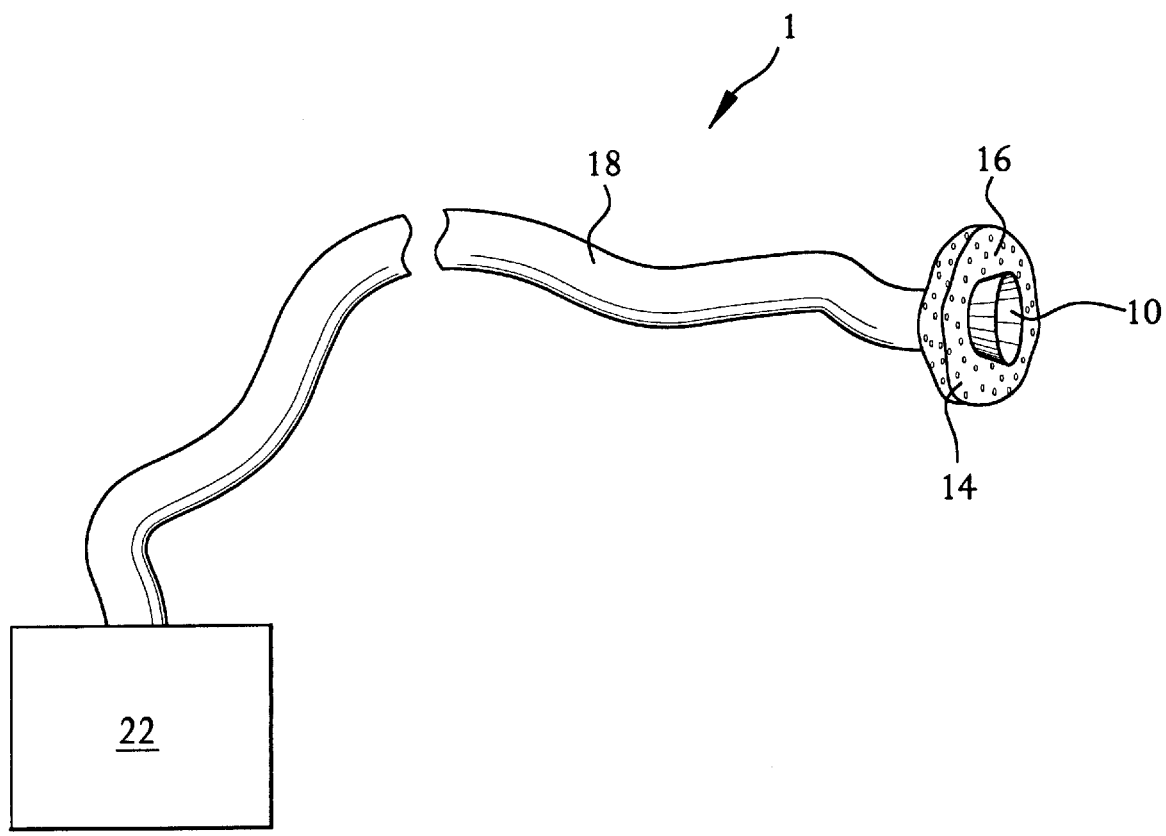

This invention relates generally to external catheters. More specifically, this invention relates to a external catheter which uses a water based adhesive for secure attachment to the genitalia area.

BACKGROUND OF THE INVENTION

Advances in medical care and treatment have extended effective projected lifespans. It is estimated that by the year 2030, there will be about 70 million older persons, more than twice their number in 1990. The most rapid increase is expected between the years 2010 and 2030 when the "baby boom" generation reaches age 65. People 65 and over are projected to represent 13% of population in the year 2000 but will be 20% by 2030. As a result of this increase in the aged population, more and more people will be placed in nursing homes and retirement communities. Many of these people will be afflicted with a variety of physical and mental ailments. While modern medical science has developed procedures and treatments to counteract a number of these illnesses and afflictions, certain more simple and basic treatment problems still remain.

For example, for many senior citizens, urinary incontinence is still a major and prevalent problem. Urinary incontinence requires the nurse or caregiver to constantly maintain and check on the patient in order to prevent further complications from arising. For example, prolonged contact with wet diapers or clothing results in rapid skin breakdown and possible infection of the patient.

To combat this problem, the present practice is to insert a catheter into the patient's bladder and change it weekly. However, after 48 hours, substantially all of patients with an indwelling catheter have greater than 100,000 colonies per milliliter of micro-organisms growing in the urine. In fact, if a virulent organism is present, urinary tract infection or even invasion of the blood stream can occur. However, without an indwelling catheter, skin breakdown and infection can occur.

With males, in the absence of urinary tract obstruction, a condom type catheter with a tube at the end can be employed. However, such a device obviously presents problems for application to the female anatomy. Previous attempts at creating external female catheters have been unsuccessful in solving the primary problems associated with catheters, namely, cost effectiveness, case of application and maintaining a leak proof seal. Since proper procedure requires that the catheter be periodically replaced, a catheter which is prohibitively priced will not be cost effective for use by nursing homes or other similar institutions. In addition, this periodic replacement also demands that the catheter be easy to apply in order to prevent cumbersome and time consuming changing periods. Finally, the maintenance of a leak proof seal with the patient is especially important in order to avoid the previously mentioned problems of infection and contamination. However, in contrast to the relatively effective condom type catheter for males, the female anatomy poses some substantial difficulties for the installation of a leak proof catheter.

Accordingly, if an effective external catheter can be devised for females, it would be a great medical benefit resulting in fewer complications for the patients and less maintenance and upkeep for the caregiver.

SUMMARY OF THE INVENTION

An external catheter for attachment to genitalia comprising a flow tube having a first and second end, the flow tube at the first end being funnel shaped, a spongy covering attached to the funnel shaped end for sealing an area around the genitalia, the spongy covering being shaped so as to conform to the area surrounding the genitalia, a skin adhesive for securing the spongy covering to the area surrounding the genitalia and a fluid collector connected to said second end of said flow tube.

A BRIEF DESCRIPTION OF THE DRAWINGS

Figure 2:
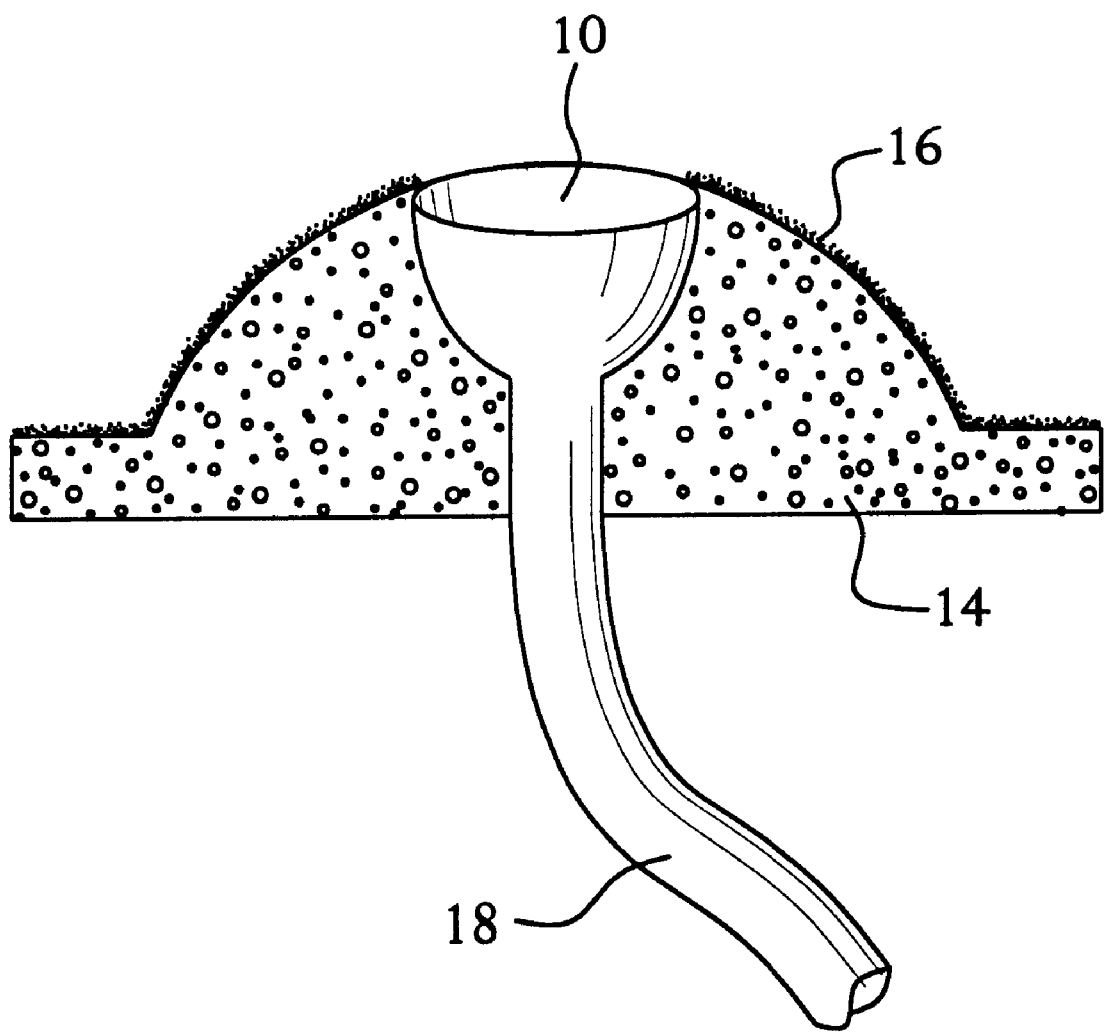
Figure 3:
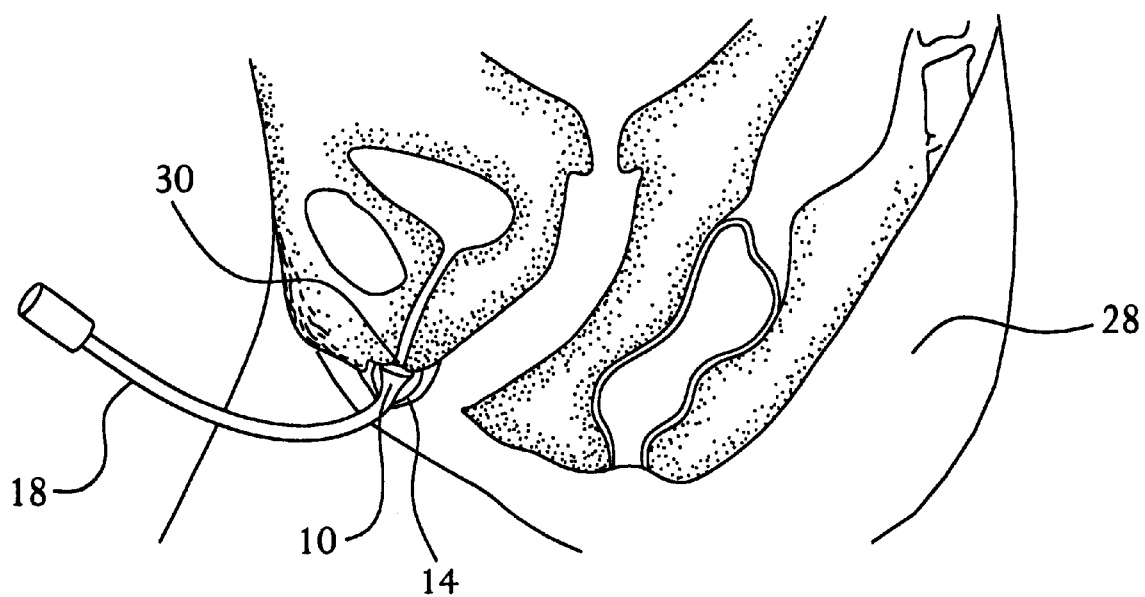
Figure 4:
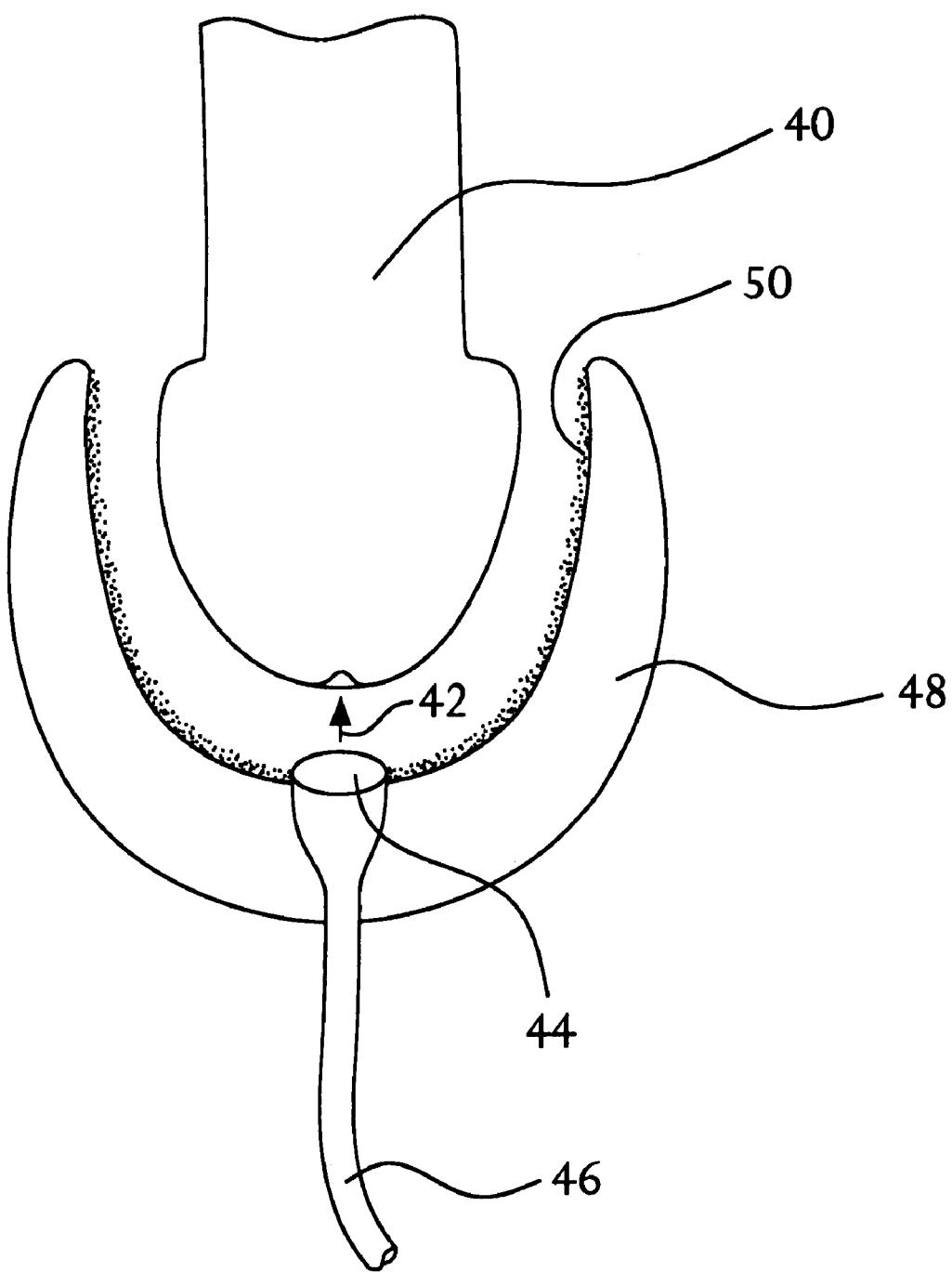

The accompanying drawings illustrate preferred embodiments of the invention according to the practical application of the principles thereof, and in which:

FIG. 1: is an illustration of an external female catheter made in accordance with the teachings of the present invention;

FIG. 2: is a front view of the external female catheter made in accordance with the teachings of the present invention;

FIG. 3: illustrates the manner of application of the external female catheter made in accordance with the teachings of the present invention; and FIG. 4: is an illustration of the catheter made in accordance with the teachings of the present invention for use by a male.

A DETAILED DESCRIPTION OF THE INVENTION

The preferred embodiment will be described with reference to the drawing figures where like numerals represent like elements throughout.

Referring to FIG. 1, there is shown an external catheter 1 made in accordance with the teachings of the present invention. The catheter 1 includes a funnel-like end portion 10, a spongy covering 14, a skin adhesive 16, a strand of flexible flow tubing 18 and a distal collection system 22.

As more clearly shown in FIG. 2, the catheter 1 is adapted for engagement with female genitalia. Specifically, the funnel-like end portion 10, spongy covering 14, and skin adhesive 16 attach directly to the area surrounding the female urethra.

It is well known that the urethra is a narrow membranous canal about an inch and a half in length, extending from the neck of the bladder to the meatus urinarius. The urethra is located beneath the symphysis pubis and imbedded in the anterior wall of the vagina with its direction is obliquely downward and forward. The urethra's diameter when undilated is approximately a quarter of an inch.

Accordingly, the funnel like portion 10 is sized to encompass the entire opening of the urethra. Surrounding the funnel-like end portion 10 is the spongy covering 14 which is shaped to cover the area immediately surrounding the urethra 30 (see FIG. 3). The spongy covering 14 will preferably cover an area including the clitoris, part of the vulva, the labia and possibly a short distance into the front of the vagina of about 2 to 3 centimeters. The spongy covering 14 is attached to the outside of the tubing 18 and the funnel-like portion 10. The spongy covering 14 may be fixedly attached to the outside of the tubing 18 or may be releasably attached to allow for ease of cleaning and storage. It is contemplated that the spongy covering 14 may also be integrally molded as a part of the tubing 18 and the funnel-like portion 10.

In the preferred embodiment, the spongy covering material is constructed of silicone and is available from the Schering-Plough Company, OTC Division in Kenilworth, N.J. 07033 under the brand name of Cushlin. The tubing 18 is common sterilized medical tubing as is known in the art and is selected to provide a contiguous and leakless transfer of fluids from the patient to a collection system 22. Preferably, the tubing is constructed of polyvinyl chloride and has an external diameter of approximately 8 millimeters. The length of the tubing varies dependent upon the application environment but lengths from approximately 4 to 6 feet in length are preferred. Such tubing is available from Medisystems Corporation, in Seattle, Wash. 98101-3016, model number LBL-BT01 REV. 11/93, M3-8630/9795. Suitable collection systems as used herein are well known in the art and typically consist of a large plastic collection bag or similar container.

The application procedure for the use of the catheter 1 will now be described with reference to FIG. 3. As a first step, it important to undertake a thorough cleansing and defollicing of the pubic area before placement of the catheter. Due to the use of adhesive, any extraneous soilure or pubic hair may compromise the seal created by the adhesive. In the preferred embodiment, the adhesive is available from ADMTronics under the trademark Pros-Aide®, model number 920Z10022 from Pegasus Laboratories, Northvale, N.J. is utilized. The Pros-Aid adhesive is FDA approved and provides a strong bond with the skin, is hypo allergenic and has high water resistance.

Next, after removing the catheter 1 from its sterile packaging, a small amount of adhesive 16, such as the Pros-Aide brand adhesive is applied to the attachment surface of the spongy covering 14 (see FIG. 2). The adhesive 16 should be spread so as to adequately cover all the surfaces of the spongy covering 14 in order to avoid any leakage during use.

The patient is then readied for application by spreading the patient's legs to facilitate placement of the catheter 1. The funnel-like portion 10 of the catheter 1 is appropriately guided to cover the urethra 30 of the patient 28. The spongy covering 14 is pressed firmly against the area surrounding the urethra region of the patient 28 and the adhesive 16 is given a sufficient amount of time to dry and seal. The spongy covering 14 will cover an area immediately surrounding the urethra including the clitoris, part of the vulva, the labia and possibly a short distance into the front of the vagina. Care must be taken not to completely cover the vaginal opening. Finally the distal end portion of the tubing 18 is connected to a collection balloon or device, not shown. The catheter 1 should then be spot tested to detect any leaks and to test the integrity of the seal. Periodic changing will then be required in order to maintain a sanitary and healthy environment.

Preferably, the catheter is applied by the caregiver, nurse or medical professional to ensure the integrity of the seal of the catheter. A small amount of mineral oil is used to clean off the skin to remove excess adhesive. Rubbing alcohol can be used to clean off the catheter itself.

Typically, the catheter is used for approximately 2 to 3 days in length before changing is required. The length will vary dependent upon a number of factors including: the amount of movement the patient undertakes during the period in which the catheter is applied, the amount of urination the patient produces and the quality of the seal which was achieved during initial application of the catheter. Removal of the catheter can be accomplished with the use of mineral oil or other similar solvents or adhesive cleansers.

While primarily designed to address the problems present with prior art catheters for females, the catheter of the present invention may also be used by males as illustrated by FIG. 4. In this embodiment, the catheter is coupled to the male penis 40. Funnel like portion 44 is dimensioned and positioned for immediate surrounding engagement as shown by arrow 42, with the meatus urinarius of the male urethra. Surrounding the funnel like portion 44 is the spongy covering 48 which is held in place by adhesive 50 to the penis 40. Tubing 46 stretches from the funnel like portion 44 to a collection balloon or device, not shown.

While the present invention has been described in terms of the preferred embodiment, other variations which are within the scope of the invention as outlined in the claims will be apparent to those skilled in the art.

What is claimed is:

1. A female external catheter for attachment to the urethra comprising:

an attachment portion for engagement with the urethra, said attachment portion having a funnel shaped receiving end sized to encompass the urethra;

a spongy covering attached to said funnel shaped receiving end for sealing the area immediately around the urethra; and a flow tube having two ends, said flow tube connected at one end to said funnel shaped receiving end.

2. The catheter of claim 1 further comprising a collection means connected to said other end of said flow tube.

3. The catheter of claim 1 further comprising a skin adhesive applied to said spongy covering for securing said spongy covering to the area immediately around the urethra, said adhesive providing a seal around the urethra.

4. The catheter of claim 1 wherein said flow tube is made from polyvinyl chloride.

5. An external catheter for attachment to the urethra comprising:

a flow tube having a first and second end, said flow tube at the first end being funnel shaped;

a spongy covering attached to said funnel shaped end, said spongy covering being shaped so as to conform to the area immediately surrounding the urethra; and collection means connected to said second end of said flow tube.

6. The catheter of claim 5 further comprising a skin adhesive applied to said spongy covering for securing said spongy covering to the area immediately around the urethra, said adhesive providing a seal around the urethra.

7. The catheter of claim 5 wherein said flow tube is made from polyvinyl chloride.

8. A method of attaching an external catheter comprising the steps of:

selecting the catheter of claim 5;

applying a skin adhesive to the spongy portion of the catheter;

positioning the spongy portion about the urethra;

pressing the spongy portion firmly about the urethra; and allowing the adhesive to firmly set.

9. A male external catheter for attachment to the penis comprising:

an attachment portion for engagement with the penis said attachment portion having a funnel shaped receiving end dimensioned for immediate surrounding engagement with the urethra of the penis;

a spongy covering attached to said funnel shaped receiving end for sealing the area around the penis; and a flow tube having two ends, said flow tube connected at one end to said funnel shaped receiving end.

10. The catheter of claim 9 further comprising a collection means connected to said other end of said flow tube.

11. The catheter of claim 9 further comprising a skin adhesive applied to said spongy covering for securing said spongy covering around the penis, said adhesive providing a seal around the urethra.

12. The catheter of claim 9 wherein said flow tube is made from polyvinyl chloride.

* * * * *